United States Patent
Mihan et al.

(10) Patent No.: US 6,995,267 B2
(45) Date of Patent: Feb. 7, 2006

(54) METHOD FOR PRODUCING CYCLOPENTADIENE COMPOUNDS

(75) Inventors: Sharam Mihan, Ludwigshafen (DE); Markus Enders, Heidelberg (DE); Gerald Kohl, Mannheim (DE)

(73) Assignee: Basell Polyolefine GmbH, Wesseling (DE)

( * ) Notice: Subject to any disclaimer, the term of this patent is extended or adjusted under 35 U.S.C. 154(b) by 272 days.

(21) Appl. No.: 10/471,540

(22) PCT Filed: Mar. 15, 2002

(86) PCT No.: PCT/EP02/02924

§ 371 (c)(1),
(2), (4) Date: Sep. 11, 2003

(87) PCT Pub. No.: WO02/074745

PCT Pub. Date: Sep. 26, 2002

(65) Prior Publication Data

US 2004/0097749 A1    May 20, 2004

(30) Foreign Application Priority Data

Mar. 20, 2001   (DE) ................................ 101 13 930

(51) Int. Cl.
*C07D 215/06*       (2006.01)

(52) U.S. Cl. ..................................... 546/173; 585/357
(58) Field of Classification Search ................ 546/173; 585/357

See application file for complete search history.

(56) References Cited

U.S. PATENT DOCUMENTS 6,063,948 A * 5/2000 Gruter et al. .................. 556/11
6,417,405 B2 * 7/2002 Shankar ....................... 568/350
2004/0242880 A1 * 12/2004 Mihan et al. .................. 546/2

FOREIGN PATENT DOCUMENTS

WO          97/42158          11/1997

OTHER PUBLICATIONS

Roczniki Chemii, 34, 1599 (1960) Mirek.
Lehrbuch der Organischen Chemie, 1957, Heterocyclen.

* cited by examiner

*Primary Examiner*—Fiona T. Powers
(74) *Attorney, Agent, or Firm*—Novak Druce & Quigg, LLP; Jason D. Voight

(57) ABSTRACT

A process for preparing substituted cyclopentadiene compounds and cyclopentadiene compounds which can be prepared thereby are described.

10 Claims, No Drawings

METHOD FOR PRODUCING CYCLOPENTADIENE COMPOUNDS

The present invention relates to a process for preparing substituted cyclopentadiene compounds.

Various methods of preparing substituted cyclopentadiene compounds are known. Many substituted cyclopentadiene compounds are prepared by addition of metal alkyls onto a cyclopenten-1-one or 1-indanone derivative. A secondary reaction which frequently occurs is deprotonation of the cyclopenten-1-ones and 1-indanones, which leads to dimeric condensation products. These condensation products then have to be separated off in a purification step. The purified addition product is then usually dehydrated to form the desired cyclopentadiene. Depending on the addition product, the dehydration requires conditions under which the substituted cyclopentadiene formed dimerizes and then has to be cracked again in a subsequent step. This synthesis is complicated and often leads to only low yields of the substituted cyclopentadiene compounds.

In the case of very bulky substituents which are less nucleophilic and more basic, the deprotonation of the cyclopenten-1-ones and 1-indanones occurs preferentially. Thus, cyclopentadiene compounds having bulky substituents are prepared using dilithioferrocene compounds onto which electrophiles are added. However, this generally leads to 1,1'- and 1-substituted ferrocenes. The cyclopentadiene compounds can then be split off directly, for example by means of elemental lithium, to form lithium cyclopentadienyl compounds which can, for example, be used directly in the synthesis of metallocenes. However, as a result of the incomplete reaction with the electrophiles, the unsubstituted starting cyclopentadiene is also obtained, so that purification is generally also carried out here.

It is an object of the present invention to find a new process for preparing substituted cycldpentadiene compounds which is simple to carry out, leads selectively to the substituted cyclopentadienyl compounds and, in particular, is also suitable for the introduction of bulky radicals.

We have found that this object is achieved by a process for preparing substituted cyclopentadiene compounds, which comprises the following steps:

(A) reacting a compound of the formula I

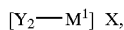

$$[Y_2\text{---}M^1]\ X,$$

I where the substituents have the following meanings:

$M^1$ is Co, Rh or Ir,

X is fluorine, chlorine, bromine, iodine, trifluorosulfonyl, tosyl,

Y are identical or different and each have the formula II

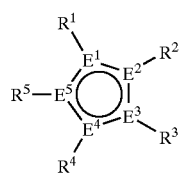

II where the variables have the following meanings:

$E^1$–$E^5$ are each carbon or at most one $E^1$ to $E^5$ is phosphorus, $R^1$–$R^5$ are each, independently of one another, hydrogen, $C_2$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, trialkylsilyl having three independent $C_1$–$C_{20}$-alkyl groups, where the organic radicals $R^1$–$R^5$ may also be substituted by halogens and/or nitrogen-, phosphorus-, sulfur- or oxygen-containing groups and two geminal or vicinal radicals $R^1$–$R^5$ may also be joined to form a five- or six-membered ring, with a compound $M^2X_nR6_{n-z}$, where the variables have the following meanings:

$R^6$ is $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, trialkylsilyl having three independent $C_1$–$C_{20}$-alkyl groups or an unsubstituted, substituted or fused, partially unsaturated heterocyclic or heteroaromatic ring system, where the organic radical $R^6$ may also be substituted by halogens and/or sulfur-, phosphorus-, nitrogen- or oxygen-containing groups, $M^2$ is Li, Na, K, Mg, Al, B, n is 0, 1 or 2 and is less than z, z is an integer corresponding to the oxidation state of $M^2$, and (B) reacting the intermediate obtained in this way with iron(III) chloride.

The cyclopentadienyl ring Y in $Y_2$-$M^1$ can also be a heterocyclopentadienyl ligand, i.e. a ring in which at least one carbon atom may be replaced by a heteroatom of group 15 or 16. In this case, preference is given to a $C_5$-ring carbon being replaced by phosphorus. It is preferred that all atoms $E^1$–$E^5$ are carbon.

Examples of possible organic radicals $R^1$–$R^6$ are: $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$–$C_{10}$-aryl group as substituent, e.g. cyclopropane, cyclobutane, cyclopentane, cyclohexane, cycloheptane, cyclooctane, cyclononane or cyclododecane, $C_2$–$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m, p-methylbenzyl, 1- or 2-ethylphenyl. In the trialkylsilyl radicals, suitable alkyl radicals are, independently of one another, the same $C_1$–$C_{20}$-alkyl groups which have been described in detail above for $R^1$–$R^6$, where two alkyl radicals may also be joined to form a 5- or 6-membered ring; examples of such trialkylsilyl radicals are trimethylsilyl, triethylsilyl, butyldimethylsilyl or tributylsilyl. The organic radicals $R^1$–$R^6$ may also be substituted by halogens such as fluorine, chlorine, bromine or iodine and/or nitrogen-, phosphorus-, sulfur- or oxygen-containing groups such as =NR, —NR$_2$, =PR, PR$_2$, —SR, =S, —OR or =O, where R is $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or trialkylsilyl having three independent $C_1$–$C_{20}$-alkyl groups as described in detail for $R^1$–$R^6$.

Two geminal or vicinal radicals $R^1$–$R^5$ may also be joined to form a five- or six-membered ring, e.g. tetrahydroindenyl, indenyl, benzindenyl or fluorenyl, and the five- or six-membered rings can also be heteroaromatic, e.g. 7-cyclopentathiophene, 7-cyclopentadipyrrole, 7-cyclopentadiphosphole, thiapentalene, 2-methylthiapentalene, azapentalene, oxapentalene, borapentalene or phosphapentalene.

Preferred radicals $R^1$–$R^5$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, naphthyl, biphenyl and anthranyl. Particular examples of organosilicon substituents are trialkylsilyl groups having from 1 to 10 carbon atoms in the alkyl radical, in particular trimethylsilyl groups. Some of the cyclopentadienyl systems used for this purpose are commercially available.

To be able to utilize the substituted cyclopentadiene compounds for the synthesis of metallocenes, it is often customary to deprotonate them by means of a strong base and to react the cyclopentadienyl anion obtained in this way with, for example, a transition metal halide. When using this method, it is advantageous for at least one of $R^1$–$R^5$ to be a hydrogen atom.

This method is particularly advantageous for starting compounds having simple and cheap Y systems. Particularly preferred radicals $R^1$–$R^5$ are therefore hydrogen, methyl or two vicinal vinylic groups which together form an aromatic six-membered ring system; in particular, $R^1$–$R^3$ are each hydrogen and $R^4$ and $R^5$ together form a fused-on aromatic ring system, so that Y is an indenyl group.

A particularly simple and inexpensive Y system is unsubstituted cyclopentadienyl in which all radicals $R^1$–$R^5$ are hydrogen, and this is therefore also particularly preferred.

The two groups Y can be identical or different. In the case of different groups Y, this is only appropriate if. $R^6$ reacts preferentially with one of the groups Y with a selectivity of over 90%. Preference is given to the two groups Y being identical, in particular with inexpensive and readily available groups Y.

X is preferably chlorine, bromine or iodine, in particular iodine.

In the process, the cationic $Y_2$-$M^1$ compounds are used. Particularly well-suited compounds are $Y_2$—Co compounds, in particular those in which X is iodine. An example of a particularly useful compound is bis(cyclopentadienyl) cobalt iodide.

$R^6$ can also be an unsubstituted, substituted or fused, heterocyclic aromatic ring system in which the ring contains not only carbon atoms but also heteroatoms selected from the group consisting of oxygen, sulfur, nitrogen and phosphorus. Examples of heteroaryl groups having a 5-membered ring in which from one to four nitrogen atoms or from one to three nitrogen atoms and/or a sulfur or oxygen atom can be present as ring atoms in addition to carbon are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,5-oxadiazol-5-yl, 1,3,4-oxadiazol-2-yl or 1,2,4-triazol-3-yl. Examples of heteroaryl groups having a 6-membered ring in which from one to four nitrogen atoms and/or a phosphorus atom can be present are 2-pyridinyl, 2-phosphabenzenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl or 1,2,4-triazin-6-yl. The heteroaryl groups having 5- and 6-membered rings can also be substituted by $C_1$–$C_{10}$-alkyl, $C_6$–$C_{10}$-aryl, alkylaryl having from 1 to 10 carbon atoms in the alkyl part and 6–10 atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thionaphthenyl, 7-thionaphthenyl, 3-indazolyl, 7-indazolyl, 2-benzimidazolyl or 7-benzamidazolyl. Examples of benzo-fused 6-membered heteroaryl groups are 2-quinolyl, 6-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl or 1-phenazyl. Nomenclature and numbering of the heterocycles have been taken from L. Fieser and M. Fieser, Lehrbuch der organischen Chemie, 3rd revised edition, Verlag Chemie, Weinheim 1957.

The process of the present invention gives very good yields even in the case of bulky radicals $R^6$. In a preferred embodiment, $R^6$ is naphthyl, biphenyl, anthranyl, o-, m-, p-methylphenyl, 2,3-, 2,4-, 2,5- or 2,6-dimethylphenyl, 2,3, 4-, 2,3,5-, 2,3,6-, 2,4,5-, 2,4,6- or 3,4,5-trimethylphenyl, benzyl, o-, m-, p-methylbenzyl, 1- or 2-ethylphenyl or an unsubstituted, substituted or fused, heteroaromatic ring system. $R^6$ is particularly preferably an unsubstituted or substituted 8-quinolyl radical.

Particularly well-suited compounds for addition onto Y are lithium compounds in which $M^2$ is Li. The lithium compounds of the preferred and particularly preferred groups $R^6$ are very particularly useful.

The reaction A) can be carried out at from −100 to 50° C. The reaction is preferably carried out at from −90 to 20° C., in particular from −90 to −50° C. Suitable solvents are aprotic solvents in which $M^2X_nR^6_{n-z}$ is readily soluble. Examples of suitable solvents are ethers such as diethyl ether, dibutyl ether, tetrahydrofuran, glyme or diglyme, aromatic hydrocarbons such as toluene or xylene or hydrocarbons such as pentane, hexane, heptane or octane, and mixtures of the various solvents. Particularly well-suited solvents are tetrahydrofuran, and mixtures of tetrahydrofuran and hexane.

$Y_2M^1X$ is reacted with $M^2X_nR^6_{n-z}$ in a molar ratio of Y (molar equivalents, based on total Y regardless of whether these are identical or different) to $R^6$ of from 1:0.1 to 1:5, preferably from 1:0.4 to 1:1, particularly preferably from 1:0.45 to 1:0.55.

The reaction B) can be carried out at from −100 to 50° C. The reaction is preferably carried out at from −90 to 20° C., in particular from −80 to −50° C. Suitable solvents are aprotic solvents in which $M^2X_nR^6_{n-z}$ is readily soluble. Examples of suitable solvents are ethers such as diethyl ether, dibutyl ether, tetrahydrofuran, glyme or diglyme, aromatic hydrocarbons such as toluene or xylene or hydrocarbons such as pentane, hexane, heptane or octane, and mixtures of the various solvents. Particularly well-suited solvents are tetrahydrofuran and mixtures of tetrahydrofuran and toluene.

The intermediate from A) is reacted with iron(III) chloride, preferably anhydrous iron(III) chloride, in a molar ratio of Fe to $M^1$ used in A) of from 1:0.5 to 1:5, preferably from 1:1 to 1:5, particularly preferably from 1:2 to 1:3.

The process of the present invention makes it possible to prepare substituted cyclopentadiene compounds cleanly and in good yields. These can subsequently be used for the synthesis of metallocenes. In particular, substituted cyclopentadiene systems which tend to dimerize can be set free at low temperatures by the iron(III) chloride and reacted further, for example deprotonated, at these temperatures. Preferred cyclopentadienyl systems are, for example, 1-(8-quinolyl)cyclopentadiene, 1-(1-naphthyl)cyclopentadiene and 1-(2-methyl-8-quinolyl)cyclopentadiene.

The following examples illustrate the invention:

All work was, unless indicated otherwise, carried out in the absence of air and moisture. Toluene and THF were dried over a column of molecular sieves or over sodium/benzophenone and distilled.

The following starting compounds were prepared by the literature methods cited:

8-bromoquinoline a) J. Mirek, Roczniki Chem. 1960, 34, 1599–1606.

Analysis

NMR samples were placed in the tube under inert gas and, if appropriate, melted. The solvent signals served as internal standard in the $^1$H- and $^{13}$C-NMR spectra and the chemical shifts were converted into chemical shifts relative to TMS. NMR measurements were carried out on a Bruker AC 200 and, in particular COSY experiments, on a Bruker AC 300.

Mass spectra were measured on a VG Micromass 7070 H and a Finnigan MAT 8230. High-resolution mass spectra were measured on Jeol JMS-700 and VG ZAB 2F instruments.

EXAMPLE 1

Preparation of 8-quinolylcyclopentadiene 6.63 g of 8-bromoquinoline (31.8 mmol) were dissolved in 100 ml of THF in a 250 ml Schlenk flask and, at −90° C., 12.8 ml of n-butyllithium solution (32 mmol, 2.5 M in hexane) were added dropwise. After stirring for 15 minutes, the dark reaction solution was added dropwise by means of a transfer syringe to a suspension of 10 g of cobalticinium iodide (31.6 mmol) in 200 ml of THF at −90° C. The red solution formed was allowed to warm to room temperature overnight and subsequently admixed with a little aluminum oxide (neutral) and the solvent was removed under reduced pressure. The crude product was subsequently chromatographed on a column of aluminum oxide (neutral) using toluene as eluant. Distilling off the solvent gave 8.15 g of (quinolylcyclopentadienyl)(η5-cyclopentadienyl)cobalt(I) (25.7 mmol, 81%) as a red solid.

1H-NMR (CDCl$_3$, 200 MHz): δ=3.16 (pq, Cp-CH); 4.87–4.93 (m, 6H C5H5 and quinoline-Cp-CH); (pt, 2H, Cp-CH); 5.29 (pt, 2H, cp-CH); 7.06–7.12 (m, 1H, H$^7$); 7.30–7.40 (m, 2H, H$^3$ and H$^6$); 7.54 (dd, $^3$J (H$^5$, H$^6$)=8.1 Hz, $^4$J (H$^5$, H$^7$)=1.5 Hz, 1H, H$^5$); 8.04 (dd, $^3$J (H$^4$, H$^3$)=8.3 Hz, $^4$J (H$^4$, H$^2$)=1.9 Hz, 1H, H$^4$); 8.94 (dd, $^3$J (H$^2$, H$^3$)=4.2 Hz, $^4$J (H$^2$, H$^4$)=1.8 Hz, 1H, H$^2$).

EI-MS: m/e (%)=317 (M+, 10); 251 (M+ −CpH, 100).

In a Schlenk flask, 2.05 g of (η4–8-quinolylcyclopentadiene)(η5-cyclopentadienyl)cobalt(I) (6.46 mmol) were dissolved in a mixture of 50 ml of toluene and 50 ml of THF and cooled to −78° C. A solution of 2.57 g of anhydrous iron(III) chloride (15.8 mmol) in 80 ml of THF at the same temperature was added dropwise by means of a transfer syringe. The reaction mixture obtained was stirred at this temperature for 1 hour and subsequently filtered at −30° C. through aluminum oxide (neutral) (30 cm, Ø 2 cm, toluene) into a 500 ml Schlenk flask which had been cooled to −78° C. The 8-quinolylcyclopentadiene obtained in this way can be converted into the corresponding aromatic, for example by means of sodium hydride, without further work-up. After taking off the solvent, 8-quinolylcyclopentadiene was isolated in a quantitative yield.

We claim:

1. A process for preparing substituted cyclopentadiene compounds, which comprises the following steps:

(A) reacting a compound of the formula I

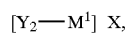

where the substituents have the following meanings:

M$^1$ is Co, Rh or Ir,

X is fluorine, chlorine, bromine, iodine, trifluorosulfonyl, tosyl,

Y are identical or different and each have the formula II

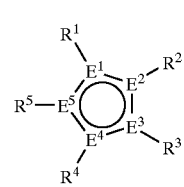

where the variables have the following meanings:

E$^1$–E$^5$ are each carbon or at most one E$^1$ to E$^5$ is phosphorus,

R$^1$–R$^5$ are each, independently of one another, hydrogen, C$_2$–C$_{20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part, trialkylsilyl having three independent C$_1$–C$_{20}$-alkyl groups, where the organic radicals R$^1$–R$^5$ may also be substituted by halogens and/or nitrogen-, phosphorus-, sulfur- or oxygen-containing groups and two geminal or vicinal radicals R$^1$–R$^5$ may also be joined to form a five- or six-membered ring, with a compound M$^2$X$_n$R$^6_{n-z}$, where the variables have the following meanings:

R$^6$ is C$_1$–C$_{20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part, trialkylsilyl having three independent C$_1$–C$_{20}$-alkyl groups or an unsubstituted, substituted or fused, partially unsaturated heterocyclic or heteroaromatic ring system, where the organic radical R$^6$ may also be substituted by halogens and/or sulfur-, phosphorus, nitrogen- or oxygen-containing groups, M$^2$ is Li, Na, K, Mg, Al, B, n is 0, 1 or 2 and is less than z, z is an integer corresponding to the oxidation state of M$^2$, and (B) reacting the intermediate obtained in this way with iron(III) chloride.

2. A process for preparing substituted cyclopentadiene compounds as claimed in claim 1, wherein M$^1$ is Co.

3. A process for preparing substituted cyclopentadiene compounds as claimed in claim 1, wherein the two groups Y are identical.

4. A process for preparing substituted cyclopentadiene compounds as claimed in claim 1, wherein at least one radical $R^1$–$R^5$ is hydrogen.

5. A process for preparing substituted cyclopentadiene compounds as claimed in claim 1, wherein all the radicals $R^1$–$R^5$ are hydrogen.

6. A process for preparing substituted cyclopentadiene compounds as claimed in claim 1, wherein $R^1$–$R^3$ are each hydrogen and $R^4$ and $R^5$ together form a fused-on aromatic ring system.

7. A process for preparing substituted cyclopentadiene compounds as claimed in claim 1, wherein $M^2$ is Li.

8. A process for preparing substituted cyclopentadiene compounds as claimed in claim 1, wherein $R^6$ is an unsubstituted, substituted or fused, heteroaromatic ring system.

9. A process for preparing substituted cyclopentadiene compounds as claimed in claim 1, wherein $R^6$ is an unsubstituted or substituted 8-quinolyl system.

10. A cyclopentadiene compound which can be prepared by a process as claimed in claim 8.

* * * * *